United States Patent [19]

Nonn

[11] Patent Number: 5,015,792
[45] Date of Patent: May 14, 1991

[54] PREPARATION OF 4,4'-DIBROMOBIPHENYL

[75] Inventor: Alain Nonn, Sainte Foy les Lyon, France

[73] Assignee: Rhone-Poulenc Chimie, Courbevoie, France

[21] Appl. No.: 341,818

[22] Filed: Apr. 24, 1989

[30] Foreign Application Priority Data

Apr. 22, 1988 [FR] France .................................. 88 05330

[51] Int. Cl.$^5$ ........................ C07C 17/12; C07C 25/18
[52] U.S. Cl. .................................... 570/208; 570/206; 570/207; 570/209
[58] Field of Search ................ 570/206, 208, 207, 209

[56] References Cited

U.S. PATENT DOCUMENTS

| 2,019,015 | 10/1935 | McCullough | 570/206 |
| 2,452,154 | 10/1948 | Ross | 570/206 |
| 2,659,760 | 11/1953 | Frevel et al. | 570/206 |
| 3,011,035 | 12/1961 | Knowles et al. | 570/206 |
| 3,062,289 | 11/1962 | Sax | 570/206 |

FOREIGN PATENT DOCUMENTS

| 0664955 | 5/1979 | U.S.S.R. | 570/206 |
| 1029874 | 5/1966 | United Kingdom | 570/206 |

OTHER PUBLICATIONS

The Condensed Chemical Dictionary Fifth Ed (1956) p. 15.

Olah et al. "Superacids" pub. Jon Wiley & Sons (1985) pp. 1-37.

Primary Examiner—Werren B. Lone
Attorney, Agent, or Firm—Burns, Doane, Swecker & Mathis

[57] ABSTRACT 4,4'-Dibromobiphenyl is selectively produced in high yields by actively brominating biphenyl in a reaction medium containing at least one strong acid having a pKa of at most 4, e.g., a carboxylic or sulfonic acid, and, optionally, a reaction solvent.

9 Claims, No Drawings

PREPARATION OF 4,4'-DIBROMOBIPHENYL

CROSS-REFERENCE TO COMPANION APPLICATION

My copending application, Ser. No. 07/341,812, filed concurrently herewith and assigned to the assignee hereof.

BACKGROUND OF THE INVENTION

1. Field of the Invention:

The present invention relates to the preparation of 4,4'-dibromobiphenyl.

2. Description of the Prior Art:

4,4'-Dibromobiphenyl is a known compound which is readily hydrolyzed into 4,4'-dihydroxybiphenyl, a useful monomer for the production of thermotropic polymers.

Various processes are known to this art for the preparation of 4,4'-dibromobiphenyl. However, serious need remains for a process permitting activation of the bromination reaction and, if possible, enhancing the 4,4'-dibromobiphenyl selectivity.

SUMMARY OF THE INVENTION

Accordingly, a major object of the present invention is the provision of an improved process for the preparation of 4,4'-dibromobiphenyl that is characterized by enhanced activity of bromination.

Briefly, the present invention features the preparation of 4,4'-dibromobiphenyl by reacting biphenyl with bromine in a reaction medium comprising at least one acid having a pKa no greater than 4.

DETAILED DESCRIPTION OF THE PREFERRED EMBODIMENTS OF THE INVENTION

More particularly according to the present invention, the subject process permits the attainment, at ambient temperature, of yields that can be in excess of 85%.

The critical characteristic of the process of the invention entails conducting the bromination reaction in a reaction medium containing a strong acid, more especially an acid having a pKa of at most 4.

In a preferred embodiment of the invention, the reaction medium comprises an acid having a pKa no greater than 1.

Typically, such acid is either a carboxylic or sulfonic acid.

Moreover, the aforesaid acids may either be unsubstituted or substituted by one or more halogen substituents, particularly fluorine substituents.

Exemplary such acids are saturated aliphatic or aromatic carboxylic acids.

Mixtures of acids may also be used.

On the other hand, in another embodiment of the invention, the bromination can be carried out in a reaction medium containing both a solvent and an acid, as described above.

Advantageously, the solvent is an aliphatic, cyclic, or aromatic hydrocarbon, or halogenated or nitro derivatives thereof. Ethers may also be used as the solvents.

Specific examples of such solvents are carbon tetrachloride, dichloromethane, 1,2-dichloroethane, o-dichlorobenzene, nitrobenzene, and the like.

In the case of an acid/solvent reaction medium, the proportion of the acid relative to the solvent may vary over a wide range. It generally is at least 5% by volume, to provide acceptable reaction kinetics.

The bromination reaction is advantageously carried out at a temperature ranging from 10° to 75° C., preferably from 20° to 50° C.

The biphenyl concentration in the reaction medium advantageously ranges from 0.1 to 3 moles/l, and preferably from 1 to 2 moles/l.

In actual practice, the bromine is typically employed in a from 0% to 20% stoichiometric excess.

Lastly, the desired 4,4'-dibromobiphenyl final product may be separated from the reaction medium by any known means.

In order to further illustrate the present invention and the advantages thereof, the following specific examples are given, it being understood that same are intended only as illustrative and in nowise limitative.

EXAMPLE 1

Into a 250 ml reactor equipped with a magnetic agitator, a reflux condenser, a dropping funnel and a thermometer, the following materials were introduced:

(i) 15.4 g biphenyl (0.1 mole);
(ii) 100 ml acid.

At ambient temperature, bromine was poured into the reactor over 10 min (35.2 g/0.22 mole) and the reaction mixture agitated for varying periods of time, always at ambient temperature.

Upon completion of the reaction, the excess bromine was consumed by sodium sulfite or bisulfate. An amount of water and dichloromethane sufficient to produce settling was added.

The organic phase was washed, dried and diluted to a given volume for CPG analysis.

The remaining operating conditions and the results are reported in the following Table:

TABLE

| Acid | pKa | Duration (hours) | Degree of Conversion (%) | Yield % by weight | | |
|---|---|---|---|---|---|---|
| | | | | 4-bromo biphenyl | 2,4'-dibromo- biphenyl | 4,4'-dibromo- biphenyl |
| $HCO_2H$ | 3.75 | 8 | 97.5 | 44.4 | 2.1 | 49.1 |
| $CF_3CO_2H$ | 0.3 | 8 | 100% | 4.8 | 8.7 | 88.2 |
| $CF_3SO_3H$ | 14 | 5 | 100% | 11.7 | 7.4 | 73.1 |

EXAMPLE 2 (COMPARATIVE)

The operating procedure of Example 1 was repeated, but acetic acid was used. The results are reported below.

| Acid | pKa | Duration (hours) | Yield % | |
|---|---|---|---|---|
| | | | 4,4'-dibromo- biphenyl | 4-bromobiphenyl |
| AcOH | 4.75 | 29 | 15 | 68 |

EXAMPLE 3

This example illustrates the embodiment of the invention in which the reaction medium contained both a solvent and an acid.

The operation was carried out as in the preceding examples by the introduction of 9.10 g (0.059 mole) biphenyl, 53 ml dichloromethane and 5.9 ml trifluoromethylsulfonic acid.

Bromine (20.75 g/0.13 mole) was poured into the reactor over 18 min at ambient temperature. The yields are reported below in % by weight.

|  | Reaction time | |
| --- | --- | --- |
|  | 5 hours | 29 hours |
| 4-bromobiphenyl | 0.4% | 0.2% |
| 2,4'-dibromobiphenyl | 5.6% | 4.5% |
| 4,4'-dibromobiphenyl | 76.8% | 90.7% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of 4,4'-dibromobiphenyl, comprising reacting biphenyl with bromine in a reaction medium which comprises at least one protic acid having a pKa no greater than 4.

2. The process as defined by claim 1, said at least one protic acid having a pKa no greater than 1.

3. The process as defined by claim 1, said at least one protic acid comprising a carboxylic or sulfonic acid.

4. The process as defined by claim 1, said at least one protic acid comprising a halogenated acid.

5. The process as defined by claim 1, said reaction medium further comprising a solvent.

6. The process as defined by claim 5, said reaction solvent comprising an aliphatic, cyclic or aromatic hydrocarbon, or a halogenated or nitro derivative thereof, or an ether.

7. The process as defined by claim 6, said reaction solvent comprising carbon tetrachloride, dichloromethane, 1,2-dichloroethane, o-dichlorobenzene or nitrobenzene.

8. The process as defined by claim 1, wherein said reaction is carried out at a temperature of from 10° to 75° C.

9. The process as defined by claim 8, wherein said temperature is from 20° to 50° C.

* * * * *